United States Patent
Kamimura et al.

(10) Patent No.: US 11,707,066 B2
(45) Date of Patent: Jul. 25, 2023

(54) DISINFECTION FORMULATION AND DISINFECTION METHOD

(71) Applicant: MITSUBISHI CHEMICAL FOODS CORPORATION, Chiyoda-ku (JP)

(72) Inventors: Ryoji Kamimura, Chiyoda-ku (JP); Kazuhisa Ohkawa, Chiyoda-ku (JP)

(73) Assignee: MITSUBISHI CHEMICAL FOODS CORPORATION, Chiyoda-ku (JP)

( * ) Notice: Subject to any disclaimer, the term of this patent is extended or adjusted under 35 U.S.C. 154(b) by 242 days.

(21) Appl. No.: 16/860,188

(22) Filed: Apr. 28, 2020

(65) Prior Publication Data
US 2020/0253202 A1    Aug. 13, 2020

Related U.S. Application Data

(63) Continuation of application No. PCT/JP2018/041941, filed on Nov. 13, 2018.

(30) Foreign Application Priority Data

Nov. 16, 2017  (JP) .................................. 2017-220780

(51) Int. Cl.
| A01N 47/46 | (2006.01) |
| A01N 33/08 | (2006.01) |
| A01N 33/12 | (2006.01) |

(52) U.S. Cl.
CPC ............. *A01N 47/46* (2013.01); *A01N 33/08* (2013.01); *A01N 33/12* (2013.01)

(58) Field of Classification Search
None
See application file for complete search history.

(56) References Cited

U.S. PATENT DOCUMENTS

| 2007/0258996 A1* | 11/2007 | Mookerjee ............. A61K 36/67 514/711 |
| 2009/0291989 A1 | 11/2009 | Mustaev et al. |
| 2016/0106701 A1 | 4/2016 | Okada et al. |

FOREIGN PATENT DOCUMENTS

| EP | 0 101 877 A1 | 3/1984 |
| JP | 58-092603 A | 6/1983 |
| JP | 06-001719 A | 1/1994 |
| JP | 7-258010 A | 10/1995 |
| JP | 2598774 B2 | 4/1997 |
| JP | 11-322521 A | 11/1999 |
| JP | 2005-112755 A | 4/2005 |
| JP | 2011-084492 A | 4/2011 |
| JP | 5455540 B2 | 3/2014 |
| JP | 2014-205625 A | 10/2014 |
| JP | 5740062 B1 | 6/2015 |
| WO | WO 2015/002264 A1 | 1/2015 |

OTHER PUBLICATIONS

"Allyl Isothiocyanate", IARC Monographs, vol. 73, pp. 37-48 (Year: 1999).*
Lin et al., "Antibacterial Mechanism of Allyl Isothiocyanate", J. Food Protect., vol. 63, No. 6, pp. 727-734 (Year: 2000).*
Torda et al., "Podusy s prekonavanim kokcidiozy u hrabavej hydiny derivatmi itk" [Experiments on the control of coccidiosis in poultry with isothiocyanate derivatives], Acta Zootechnica, vol. 21, pp. 173-184, English Abstract (Year: 1970).*
International Search Report dated Feb. 5, 2019 in PCT/JP2018/041941 filed on Nov. 13, 2018 (with English Translation), 5 pages.
Masuda et al., "Particular applications with antimicrobial effects of wasabi mustard oils in various fields", Aroma Research vol. 11, No. 2, 2010, 6 pages (with English Abstract).
Arranz, et al., Effects of organosulfurs, isothiocyanates and vitamin C towards hydrogen peroxide-induced oxidative DNA damage (strand breaks and oxidized purines/pyrimidines) in human hepatoma cells, Chemico-Biological Interactions, vol. 169, No. 1, 2007, pp. 63-71.
Kinae, et al., "Studies on Functional Properties of Sawa-wasabi (*Wasabi japonica*)", Food & Food Ingredients Journal of Japan, vol. 192, 2001 , 9 pages (with English Abstract).
Extended European Search Report dated Nov. 23, 2020 in European Patent Application No. 18877567.0, 9 pages.
Estela Quiroz-Castañeda, R., et al., "Control of Avian Coccidiosis: Future and Present Natural Alternatives" BioMed Research International, vol. 2015, No. 430610, Feb. 17, 2015, XP055728134, pp. 1-11.
Kowalska, D., et al., "Performance Indicators, Health Status and Coccidial Infection Rates in Rabbits Fed Diets Supplemented with White Mustard Meal", Ann. Anim. Sci., vol. 11, No. 3, Mar. 1, 2011, XP55749432, pp. 425-432 with cover page.
Ola-Fadunsin, S.D., et al., "Direct effects of *Moringa oleifera* Lam (Moringaceae) acetone leaf extract on broiler chickens naturally infected with *Eimeria* species", Tropical Animal Health and Production, vol. 45. No. 6, Feb. 26, 2013, XP55749446, pp. 1423-1428.
Adamu, M., et al., "Effect of *Lepidium sativum* L. (Garden Cress) Seed and Its Extract on Experimental *Eimeria tenella* Infection in Broiler Chickens", Kasetsart J. (Nat. Sci.), vol. 48, Jan. 1, 2014, XP55749514, pp. 28-37.
Combined Chinese Office Action and Search Report dated Mar. 26, 2021 in corresponding Chinese Patent Application No. 201880071765.0 (with English Translation and English Translation of Category of Cited Documents), 14 pages.
M Torda et al., "Experiments on the Control of Coccidiosis in Poultry with Isothiocyanate Derivatives", Acta Zootechnica, 1970, pp. 173-184 (with English Abstract).

* cited by examiner

Primary Examiner — Bethany P Barham
Assistant Examiner — Barbara S Frazier
(74) Attorney, Agent, or Firm — Oblon, McClelland, Maier & Neustadt, L.L.P.

(57) ABSTRACT

An anticoccidial disinfection formulation containing a compound represented by general formula (I) below as an active ingredient:

$$R_1-N=C=S \qquad (I)$$

[In formula (I), $R_1$ represents an alkenyl group having 2 to 8 carbon atoms or the like] This compound has a high sporulation inhibitory activity against coccidian oocysts and is thus effective for eradicating coccidians and for disinfecting rearing facilities and rooms of host animals, such as a livestock barn and a poultry house.

8 Claims, No Drawings

DISINFECTION FORMULATION AND DISINFECTION METHOD

TECHNICAL FIELD

The present invention relates to an anticoccidial disinfection formulation that contains an isothiocyanate compound and the like as active ingredients, and a disinfection method.

BACKGROUND ART

Coccidia are protozoa of the phylum Apicomplexa in the subkingdom Protozoa and include many pathogens for disease in humans, domestic animals, and domestic fowls. Mainly, protozoa of the genera *Eimeria* and *Isospora* (scientific names: "*Eimeria*" and "*Isospora*") in the family Eimeriidae and genus *Cryptosporidium* (scientific name: "*Crypptosporidium*") in the family Cryptosporidiidae are included in coccidians; in addition, protozoa of the genus *Sarcocystis* (scientific name: "*Sarcocystis*"), the genus *Toxoplasma* (scientific name: "*Toxoplasma*"), the genus *Besnoitia*, the genus *Hammondia*, etc., in the family Sarcocystidae are also classified as coccidians.

In general, coccidians have the following life cycle.

First, coccidian oocysts are excreted from a host. The oocysts immediately after excretion are single-celled, but undergo meiosis and develop outside the body of the host and turn into sporulated oocysts that can infect hosts. One sporulated oocyst has four sporocysts formed therein, and each sporocyst contains two sporozoites.

Next, once the sporulated oocysts are picked up by a host, sporozoites are released inside the body of the host, migrate to the sites of development, and develop into trophozoites and then into merozoites by division (asexual reproduction).

Next, the merozoites invade new cells and form gametocytes, and then the gametocytes differentiate and develop into male and female cells. The male and female cells fuse to form zygotes (sexual reproduction), and a thick membrane is formed around each zygote to form an oocyst.

Oocysts are then excreted from the body of the host together with feces.

Coccidiosis in cattle mainly occurs due to infection with protozoa of the genus *Eimeria*, such as *E. zuernii* and *E. bovis*, and results in symptoms such as bloody diarrhea. Cryptospolidiosis in cattle is also a disease caused by coccidians, and occurs due to infection with *C. parvum*. The cardinal symptom of this disease is diarrhea and the like, and this disease also infects swine, humans, etc., in addition to cattle.

Coccidiosis in swine occurs due to infection with *I. suis*, and protozoa of the genus *Eimeria*, the genus *Cryptosporidium*, etc. For example, in coccidiosis caused by *I. suis*, clinically, yellow diarrhea from suckling piglets and the like are observed.

Coccidiosis in chickens is one of the representative examples of poultry diseases, and has a large economic impact on the chicken industry. Coccidiosis in chickens mainly occurs due to infection with protozoa of the genus *Eimeria*, such as *E. tenella*, *E. necatrix*, *E. acervulina*, and *E. maxima*, and results in hemorrhagic enteritis, diarrhea, etc. Many cases that accompany bleeding result in death.

Coccidiosis in dogs occurs by infection with protozoa of the genus *Isospora* such as *I. canis*, *I. ohioensis*, *I. heydorni*, and *I. burrowsi*, and the genus *Sarcocystis*. Coccidiosis in cats occurs by infection with protozoa of genus *Isospora*, such as *I. felis* and *I. rivolta*, *T. gondii* (protozoa of the genus *Toxoplasma*), *H. hammondi* (protozoa of the genus *Hammondia*), protozoa of the genus *Besnoitia*, such as *B. wallacei* and *B. besnoiti*, and protozoa of the genus *Sarcocystis*, etc. Coccidiosis in cats and dogs results in symptoms such as water-soluble diarrhea, and some cases that accompany bloody stool and debilitation may result in death.

In addition, there are many coccidia that infect experimental animals such as rabbits, rats, mice, and guinea pigs, thereby possibly inflicting economical damage on the experimental animal industry.

Diseases caused by coccidians occur in various animals, and there are many severe cases and large economic losses; thus, it is desirable to control, as much as possible, the occurrence of coccidiosis and transmission and spread of the pathogens.

To prevent coccidiosis, rearing facilities and rooms must be cleaned, washed with water, dried, and thermally sterilized, appropriate processing of feces and the like must be enforced, and, at the same time, effective disinfectants are needed.

Since coccidia exist as oocysts outside the body of the host and the oocysts become infectious as they develop into sporulated oocysts, killing and removing the oocysts is the fundamental preventive measures. However, oocysts are highly resistant to environmental conditions, chemicals, and the like and are difficult to remove with disinfectants commonly used to control general bacteria and viruses.

To combat coccidiosis, orthodichlorobenzene formulations are widely used.

PTL 1 discloses a method for disinfecting a poultry house or a livestock barn, the method involving using, as a disinfectant, a mixture formulation containing an orthodichlorobenzene formulation and a glutaraldehyde formulation.

PTL 2 discloses a sterilizing and disinfecting agent for preventing coccidiosis in animals, the agent containing o-dichlorobenzene and dialkyldimethylammonium chloride.

PTL 3 discloses a hairy wart disease prevention and treatment method involving administering allyl isothiocyanate to the foot of hoofed animals. PTL 4 discloses a nematicide containing dichlorodiisopropyl ether and methyl isothiocyanate.

PTL 1: Japanese Patent No. 5455540
PTL 2: Japanese Patent No. 2598774
PTL 3: Japanese Patent No. 5740062
PTL 4: Japanese Unexamined Patent Application Publication No. 58-92603

SUMMARY OF INVENTION

To control coccidiosis, a disinfectant with high efficacy is needed.

An object of the present invention is to provide a disinfecting means having higher efficacy against coccidians.

The inventor of the present invention has found that isothiocyanate compounds, such as allyl isothiocyanate, have a high sporulation inhibitory activity against coccidian oocysts.

The summary of the present invention is as follows.

[1] An anticoccidial disinfection formulation comprising a compound represented by general formula (I) below as an active ingredient:
[Chem. 1]

$$R_1\text{—}N\text{=}C\text{=}S \qquad (I)$$

[In formula (I), $R_1$ represents an alkenyl group having 2 to 8 carbon atoms, an alkyl group having 1 to 6 carbon atoms, an aryl group having 6 to 12 carbon atoms, an aralkyl group having 7 to 20 carbon atoms, or a cycloalkyl group having 3 to 6 carbon atoms.]

[2] The anticoccidial disinfection formulation according to [1], wherein, in formula (I), $R_1$ represents an alkenyl group having 2 to 6 carbon atoms.

[3] The anticoccidial disinfection formulation according to [1] or [2], wherein the compound represented by general formula (I) is allyl isothiocyanate.

[4] The anticoccidial disinfection formulation according to any one of [1] to [3], wherein the anticoccidial disinfection formulation is used to disinfect a poultry house or a livestock barn.

[5] A disinfection formulation comprising a compound represented by general formula (I) below and a compound represented by general formula (II) below that are mixed as active ingredients:

[Chem. 2]

$$R_1-N=C=S \quad (I)$$

[In formula (I), $R_1$ represents an alkenyl group having 2 to 8 carbon atoms, an alkyl group having 1 to 6 carbon atoms, an aryl group having 6 to 12 carbon atoms, an aralkyl group having 7 to 20 carbon atoms, or a cycloalkyl group having 3 to 6 carbon atoms.]

[Chem. 3]

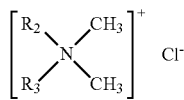

(II)

[In formula (II), $R_2$ and $R_3$ each represent an alkyl group having 8 to 16 carbon atoms, and may be the same as or different from each other.]

[6] A method for disinfecting a poultry house or a livestock barn against coccidia, the method comprising using the disinfection formulation according to any one of [1] to [5].

[7] A disinfection method against coccidia, the method comprising using a compound represented by general formula (I) below as an active ingredient:

[Chem. 4]

$$R_1-N=C=S \quad (I)$$

[In formula (I), $R_1$ represents an alkenyl group having 2 to 8 carbon atoms, an alkyl group having 1 to 6 carbon atoms, an aryl group having 6 to 12 carbon atoms, an aralkyl group having 7 to 20 carbon atoms, or a cycloalkyl group having 3 to 6 carbon atoms.]

[8] The disinfection method against coccidia according to [7], wherein, in formula (I), $R_1$ represents an alkenyl group having 2 to 6 carbon atoms.

[9] The disinfection method against coccidia according to [7] or [8], wherein the compound represented by general formula (I) is allyl isothiocyanate.

[10] The disinfection method against coccidia according to any one of [7] to [9], wherein the disinfection method is used to disinfect a poultry house or a livestock barn.

[11] Use of a compound represented by general formula (I) below as an anticoccidial disinfection formulation:

[Chem. 5]

$$R_1-N=C=S \quad (I)$$

[In formula (I), $R_1$ represents an alkenyl group having 2 to 8 carbon atoms, an alkyl group having 1 to 6 carbon atoms, an aryl group having 6 to 12 carbon atoms, an aralkyl group having 7 to 20 carbon atoms, or a cycloalkyl group having 3 to 6 carbon atoms.]

[12] The use of the compound as an anticoccidial disinfection formulation according to [11], wherein, in formula (I), $R_1$ represents an alkenyl group having 2 to 6 carbon atoms.

[13] The use of the compound as an anticoccidial disinfection formulation according to [11] or [12], wherein the compound represented by general formula (I) is allyl isothiocyanate.

[14] The use of the compound as an anticoccidial disinfection formulation according to any one of [11] to [13], wherein the compound is used to disinfect a poultry house or a livestock barn.

Advantageous Effects of Invention

Since a particular isothiocyanate compound according to the present invention has a high sporulation inhibitory activity against coccidian oocysts, the compound can effectively prevent the stage in which the oocysts excreted from the body of the host develop into sporulated oocysts and become infective.

Thus, this isothiocyanate compound is effective for killing coccidians, and is effective for anticoccidial disinfection of the rearing facilities and rooms, for example, livestock barns and poultry houses, of host animals.

According to the present invention, occurrence of the coccidiosis and the transmission and spread of the pathogens can be effectively controlled.

DESCRIPTION OF EMBODIMENTS

<Anticoccidial Disinfection Formulation>

The present invention encompasses all of anticoccidial disinfection formulations that contain a compound represented by general formula (I) below (hereinafter, this compound may be referred to as a "compound (I)").

"Anticoccidial disinfection" means disinfection against coccidia, in other words, killing coccidia or depriving coccidia of their infectability.

"Anticoccidial disinfection formulation" means a formulation used for disinfection against coccidia, in other words, a formulation used to kill coccidia or deprive coccidia of their infectability.

[Chem. 6]

$$R_1-N=C=S \quad (I)$$

In general formula (I) above, $R_1$ represents an alkenyl group having 2 to 8 carbon atoms, an alkyl group having 1 to 6 carbon atoms, an aryl group having 6 to 12 carbon atoms, an aralkyl group having 7 to 20 carbon atoms, or a cycloalkyl group having 3 to 6 carbon atoms.

The alkenyl group having 2 to 8 carbon atoms representing $R_1$ may be a linear or branched unsaturated hydrocarbon group having 2 to 8 carbon atoms having one double bond. Examples of such a group include a vinyl group, a 1-propenyl group, an allyl group (2-propenyl group), a butenyl group, a pentenyl group, a hexenyl group, a heptenyl group, and an octenyl group.

The alkyl group having 1 to 6 carbon atoms representing $R_1$ may be a linear or branched lower alkyl group having 1 to 6 carbon atoms. Examples of such a group include a methyl group, an ethyl group, an n-propyl group, an isopropyl group, an n-butyl group, an isobutyl group, a sec-butyl group, a tert-butyl group, an n-pentyl group, and an n-hexyl group.

Examples of the aryl group having 6 to 12 carbon atoms representing $R_1$ include a phenyl group, an o-tolyl group, an m-tolyl group, a p-tolyl group, a xylyl group (including all positional isomers thereof), a trimethylphenyl group (including all positional isomers thereof), a tetramethylphenyl group (including all positional isomers thereof), a 1-naphthyl group, a 2-naphthyl group, a biphenyl group, a methylnaphthyl group (including all positional isomers thereof), and dimethylnaphthyl group (including all positional isomers thereof).

Examples of the aralkyl group having 7 to 18 carbon atoms representing $R_1$ include the aforementioned lower alkyl groups but with one hydrogen atom being substituted with any of the aryl groups described above. Examples of such a group include a benzyl group, a phenethyl group, a phenylpropyl group, a 1-naphthylmethyl group, a 2-naphthylmethyl group, a 1-naphthylethyl group, a 2-naphthylethyl group, a biphenylmethyl group, and a biphenylethyl group.

Examples of the cycloalkyl group having 3 to 6 carbon atoms representing $R_1$ include a cyclopropyl group, a cyclobutyl group, a cyclopentyl group, and a cyclohexyl group.

Among these, in formula (I) mentioned above, $R_1$ preferably represents an alkenyl group having 2 to 6 carbon atoms and most preferably represents an allyl group. The compound (I) is most preferably allyl isothiocyanate.

The compound (I) has a sporulation inhibitory activity against general coccidian oocysts such as *E. zuernii, E. bovis, E. tenella, E. necatrix, E. acervulina,* and *E. maxima* of the genus *Eimeria* (scientific name: "*Eimeria*") in the family Eimeriidae, *I. suis, I. canis, I. ohioensis, I. heydorni, I. burrowsi, I. felis,* and *I. rivolta* of the genus *Isospora* (scientific name: "*Isospora*") in the family Eimeriidae, *C. parvum* of the genus *Cryptosporidium* (scientific name: "*Crypptosporidium*") in the family Cryptosporidiidae, protozoa of the genus *Sarcocystis* (scientific name: "*Sarcocystis*") in the family Sarcocystidae, *T. gondii* of the genus *Toxoplasma* (scientific name: "*Toxoplasma*") in the family Cryptosporidiidae, *B. wallacei* and *B. besnoiti* of the genus *Besnoitia* in the family Cryptosporidiidae, and *H. hammondi* of the genus *Hammondia* in the family Cryptosporidiidae.

The anticoccidial disinfection formulation of the present invention can be employed in a wide variety of known forms, such as solid forms (for example, powder, granules, and tablets) and liquid forms (for example, liquid agents and suspension agents). For example, a solid formulation may be dissolved in a solvent to prepare a disinfection solution at the time of use, and used. Alternatively, the formulation may be prepared as a liquid formulation in advance, and at the time of use, the liquid formulation may be appropriately diluted and used as a disinfection solution.

A known solvent can be employed, as appropriate, to dissolve the compound (I). For example, an appropriate solvent can be selected from water, vegetable oil, liquid animal oil, phosphate buffer solutions, carbonate buffer solutions, saline, alcohol, propylene glycol, polyethylene glycol, methyl cellulose, acetone, and dimethyl sulfoxide (DMSO), etc.

Depending on the purpose, usage, dosage form, etc., an excipient, a disintegrant, a binder, a lubricant, a coating agent, a stabilizer, a solid carrier, a buffer, a tonicity agent, a surfactant, a preservative, an antibacterial agent, an antioxidant, a pH adjuster, a dispersing agent, a deodorant, a coloring agent, a thickener, and the like may be added, as appropriate, to the anticoccidial disinfection formulation of the present invention.

Examples of the excipient include sugar alcohols (for example, erythritol, mannitol, xylitol, and sorbitol), sugars (for example, sucrose, powdered sugar, lactose, and glucose), cyclodextrins (for example, α-cyclodextrin, β-cyclodextrin, γ-cyclodextrin, hydroxypropyl β-cyclodextrin, and sulfobutyl ether β-cyclodextrin sodium), celluloses (for example, crystalline cellulose, microcrystalline cellulose, powdered cellulose, hydroxypropyl cellulose, low-substituted hydroxypropyl cellulose, ethyl cellulose, and methyl cellulose), starches (for example, corn starch, potato starch, wheat starch, rice starch, partially gelatinized starch, and gelatinized starch), dextrin, maltodextrin, sucrose ester, povidone, hypromellose phthalate, hydroxypropylmethyl cellulose acetate succinate, magnesium aluminate metasilicate, synthetic aluminum silicate, light anhydrous silicic acid, calcium silicate, carmellose sodium, hypromellose, gum arabic, sodium alginate, gelatin, pullulan, polyvinyl alcohol, and carboxyvinyl polymers.

Examples of the disintegrant include crospovidone, carmellose, carmellose calcium, croscarmellose sodium, low-substituted hydroxypropyl cellulose, sodium starch glycolate, corn starch, potato starch, wheat starch, rice starch, partially gelatinized starch, gelatinized starch, carboxymethyl starch sodium, agar, and gelatin powder.

Examples of the binder include hydroxypropyl cellulose, carboxymethyl cellulose, ethyl cellulose, methyl cellulose, carmellose sodium, and polyvinylpyrrolidone.

Examples of the lubricant include stearic acid, magnesium stearate, calcium stearate, talc, hydrous silicon dioxide, light anhydrous silicic acid, sucrose fatty acid ester, hydrogenated vegetable oil, and macrogol.

Examples of the coating agent include sucrose, hydroxypropyl cellulose, hydroxypropylmethyl cellulose, gelatin, glycerin, sorbitol, ethyl cellulose, polyvinylpyrrolidone, cellulose acetate phthalate, hydroxypropylmethyl cellulose phthalate, acrylic acid-methacrylic acid copolymers, aminoalkyl methacrylate copolymer E, aminoalkyl methacrylate copolymer RS, cellulose acetate phthalate, methacrylic acid copolymer L, methacrylic acid copolymer LD, and methacrylic acid copolymer S.

Examples of the stabilizer include fatty acids and salts thereof, methylparaben, parahydroxybenzoates (for example, propylparapene), alcohols such as chlorobutanol, pentyl alcohol, benzyl alcohol, and phenylethyl alcohol, thimerosal, acetic anhydride, sorbic acid, sodium hydrogen sulfite, L-ascorbic acid, sodium ascorbate, butylhydroxyanisole, butylhydroxytoluene, propyl gallate, tocopherol acetate, gentisic acid, ascorbic acid, tocopherol, gallic acid, gallates, α-thioglycerol, α-tocopherol, proteins, and polysaccharides.

Examples of the solid carrier include natural mineral powder (for example, cationic clay, virophilite clay, bentonite, montmorillonite, kaolin, clay, talc, chalk, quartz, attapulgite, and diatomaceous earth), synthetic mineral powder (for example, silicic acid, alumina, and silicates), and natural polymers (for example, crystalline cellulose, corn starch, gelatin, and alginic acid)

Examples of the buffer include buffer solutions such as phosphates, acetates, carbonates, citrates, tartrates, trishydroxymethylaminomethane, and 4-(2-hydroxyethyl)-1-piperazineethanesulfonic acid (HEPES).

Examples of the tonicity agent include sodium chloride, glucose, D-sorbitol, glycerin, and D-mannitol.

Examples of the surfactant include nonionic surfactants (for example, aliphatic alcohol ethoxylate, polyoxyethylene alkyl phenyl ether, alkyl glycoside, fatty acid alkanolamide, polyoxyethylene castor oil, hydrogenated castor oil, octyl glucoside, peptyl thioglucoside, decanoyl-N-methylglucamide, polyoxyethylene dodecyl ether, polyoxyethylene heptamethylhexyl ether, polyoxyethylene isooctyl phenyl ether, polyoxyethylene nonyl phenyl ether, polyoxyethylene fatty acid ester, sucrose fatty acid ester, and polyoxyethylene sorbitol ester), anionic surfactants (for example, sodium dodecyl sulfate, sodium dodecyl sulfonate, sodium dodecyl benzene sulfonate, sodium dodecyl-N-sarcosinate, sodium cholate, sodium deoxycholate, sodium taurodeoxycholate, hydrogenated coconut fatty acid sodium monoglyceride monosulfate, sodium α-olefin sulfonate, sodium N-palmitoyl glutamate, and sodium N-methyl-N-acyltaurine), cationic surfactants (for example, lauryl trimethyl ammonium chloride, stearyl trimethyl ammonium chloride, benzethonium chloride, cetyl pyridinium chloride, benzalkonium chloride, stearyl dimethyl benzyl ammonium chloride, cetyl trimethyl ammonium bromide, tetradecyl ammonium bromide, and dodecyl pyridinium chloride), and ampholytic surfactants (palm oil fatty acid amidopropyl betaine, lauryl dimethylamino acetate betaine, lauryl dimethylamine oxide, 2-alkyl-N-carboxymethyl-N-hydroxyethyl imidazolium betaine, N-lauryl diaminoethyl glycine, N-myristyl diaminoethyl glycine, N-alkyl-1-hydroxyethylimidazoline betaine sodium, 3-[(3-cholamidopropyl)dimethylammonio]-1-propanesulfonic acid, 3-[(3-cholamidopropyl)dimethylammonio]-2-hydroxy-1-propanesulfonic acid, palmitoyl lysolecithin, dodecyl-N-betaine, and dodecyl-β-alanine).

Examples of the preservative include parabens (for example, sodium benzoate, methyl paraben, ethyl paraben, propyl paraben, and butyl paraben), cetylpyridinium chloride, alkyldiaminoethylglycine hydrochloride, potassium sorbate, thimerosal, parahydroxybenzoates, methyl paraoxybenzoate, phenoxyethanol, chlorobutanol, benzyl alcohol, phenethyl alcohol, and dehydroacetic acid.

Examples of the antibacterial agent include quaternary ammonium salt-based germicidal disinfectants (for example, benzalkonium chloride and benzethonium chloride), phenol-based germicidal disinfectants (for example, 3-methyl-4-isopropylphenol and thymol), chlorohexidine, triclosan, cetylpyridinium chloride, zinc gluconate, zinc citrate, and extract and essential oil of antibacterial plants (for example, thyme, lemongrass, citrus, lemon, orange, anise, clove, aniseed, pine, cinnamon, geranium, rose, mint, lavender, citronella, eucalyptus, peppermint, camphor, ajowan, sandalwood, rosemary, black pine, freegrass, lemongrass, latania, and cedar).

Examples of the antioxidant include sulfite and ascorbic acid.

Examples of the pH adjustor include acids such as hydrochloric acid, carbonic acid, acetic acid, citric acid, phosphoric acid, boric acid, and sulfuric acid, alkaline metal hydroxides such as sodium hydroxide, potassium hydroxide, calcium hydroxide, and magnesium hydroxide, alkaline metal carbonates such as sodium carbonate, hydrogen carbonates, alkaline metal acetates such as sodium acetate, alkaline metal citrates such as sodium citrate, bases such as trometamol, and amines such as monoethanolamine and diisopropanolamine.

Examples of the dispersing agent include sodium carboxymethyl cellulose, hydroxypropylmethyl cellulose, polyvinylpyrrolidone, and polysorbate 80 (TWEEN 80).

Examples of the deodorant include fragrance ingredients (for example, 1-carvone, cinnamic aldehyde, orange oil, methyl salicylate, eugenol, menthyl acetate, spiranthol, ethyl acetate, ethyl butyrate, isoamyl acetate, hexanal, hexenal, methyl anthranilate, ethyl methyl phenyl glycidate, benzaldehyde, vanillin, ethyl vanillin, furaneol, maltol, ethyl maltol, gamma/delta decalactone, gamma/delta undecalactone, N-ethyl-p-menthan-3-carboxamide, menthyl lactate, and ethylene glycol-1-menthyl carbonate), natural essential oil (for example, winter green oil, clove oil, thyme oil, sage oil, cardamon oil, rosemary oil, marjoram oil, nutmeg oil, lavender oil, and para cress oil), fruit-based fragrance ingredients (for example, lemon, orange, grapefruit, apple, banana, strawberry, blueberry, melon, peach, pineapple, grape, muscat, cherry, and squash), pepper mint, spearmint, menthol, yogurt, coffee, and brandy.

Examples of the coloring agent include caramel pigments, gardenia pigments, anthocyanin pigments, annatto pigments, paprika pigments, safflower pigments, red malt pigments, carotene pigments, carotenoid pigments, flavonoid pigments, cochineal pigments, amaranth (red No. 2), erythrosine (red No. 3), allura red AC (red No. 40), new coccin (red No. 102), phloxine (red No. 104), rose bengal (red No. 105), acid red (red No. 106), tartrazine (yellow No. 4), sunset yellow FCF (yellow No. 5), fast green FCF (green No. 3), brilliant blue FCF (blue No. 1), indigo carmine (blue No. 2), blue No. 201, blue No. 204, copper chlorophyll, copper chlorophyrin sodium, titanium dioxide-coated mica, and titanium oxide.

Examples of the thickener include sodium alginate, propylene glycol alginate, locust bean gum, guar gum, sodium caseinate, egg albumin, gelatin agar, starch, processed starch, carboxymethyl cellulose calcium, carboxymethyl cellulose sodium, carboxyvinyl polymer, methyl cellulose, ethyl cellulose, hydroxyethyl cellulose, hydroxypropyl cellulose, hydroxypropylmethyl cellulose, carmellose sodium, sodium polyacrylate, polyvinylpyrrolidone, hypromellose, sodium hyaluronate, chondroitin sodium sulfate, sugar alcohols (sorbitol, xylitol, maltitol, lactitol, etc.), polyhydric alcohols (glycerin, propylene glycol, polyethylene glycol, polyvinyl alcohol, etc.), polyvinylpyrrolidone, sodium starch glycolate, sodium starch phosphate, xanthan gum, carrageenan gum, tragacanth gum, quince seed extract, and sodium chondroitin sulfate.

By using the anticoccidial disinfection formulation of the present invention for a disinfection subject or a disinfection subject area, sporulation of the coccidian oocysts that are present in the subject or the area can be inhibited, and the coccidia can be effectively eradicated.

The disinfection subject is basically all articles, places, and areas contaminated or possibly contaminated with coccidia and is not particularly limited. For example, the present invention can be applied to perform anticoccidial disinfection on livestock production facilities such as livestock barns, poultry houses, and livestock insemination facilities, healthcare and nursing care facilities and areas, animal rearing facilities and areas that contain experimental animals and domestic animals, meat production and processing facilities, floors, walls, and doorways of food production and processing facilities, articles installed or placed in these facilities, and tools and machines used in the operation in these facilities.

For example, a liquid anticoccidial disinfection formulation of the present invention is prepared in advance or at the time of use as a disinfection solution, and anticoccidial disinfection may be performed by dipping the disinfection subject into the disinfection solution or wiping the disinfection subject or the disinfection subject area with a cloth saturated with the disinfection solution. The disinfection solution may be sprayed, atomized with an atomizer, or foamed by using a foaming nozzle or the like so as to disinfect the disinfection subject or the disinfection subject area against coccidia. Alternatively, for example, a powder-form anticoccidial disinfection formulation of the present invention may be directly sprayed toward the disinfection subject or the disinfection subject area.

For example, when the floors and walls of the disinfection subject facilities and the articles installed or placed in these facilities are to be disinfected against coccidia, the disinfection subject or area may be wiped with a cloth saturated with the disinfection solution of the present invention, or the disinfection solution or the powder formulation of the present invention may be atomized and substantially evenly sprayed toward the disinfection subject or area by using a sprayer or may be foamed and sprayed by using a foaming nozzle or the like.

Alternatively, a footbath containing the disinfection solution of the present invention may be placed at the doorway of each facility so that the foot of people entering and exiting the facility are disinfected against coccidia.

When the tools and machines used in the operation in the facilities are to be disinfected against coccidia, these tools and machines may be dipped into the disinfection solution of the present invention, or the disinfection solution or the powder formulation of the present invention may be atomized and substantially evenly sprayed toward these tools and machines or may be foamed and sprayed by using a foaming nozzle or the like.

When the anticoccidial disinfection formulation of the present invention is a liquid formulation or is used after preparing into a liquid formulation, the concentration of the compound (I) in the disinfection solution is preferably 1 to 50,000 mg/L, more preferably 10 to 20,000 mg/L, yet more preferably 100 to 10,000 mg/L, still more preferably 150 to 5,000 mg/L, and most preferably 200 to 1,000 mg/L in terms of the final concentration (the concentration at the time of use).

When the anticoccidial disinfection formulation of the present invention is used as a solid formulation, the formulation preferably contains 1 to 100 wt %, more preferably 3 to 50 wt %, and most preferably 5 to 30 wt % of the compound (I).

The anticoccidial disinfection formulation of the present invention is to at least contain the compound (I) at a particular concentration, and may further contain ingredients, other than the compound (I), that are effective for anticoccidial disinfection and/or ingredients that are effective for disinfection against pathogens other than coccidia.
<Disinfection Formulation>

The present invention encompasses all of disinfectant formulations that contain the compound (I) and a compound represented by general formula (II) below (hereinafter, this compound may be referred to as a "compound (II)") as active ingredients.

The "disinfection formulation" means a formulation used eradicate pathogenic microorganisms or deprive them of their infectability.

[Chem. 7]

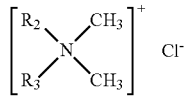

(II)

The compound (II) is dialkyldimethylammonium chloride, and, in general formula (II) above, $R_2$ and $R_3$ each represent an alkyl group having 8 to 16 carbon atoms and may be the same as or different from each other.

The alkyl group having 8 to 16 carbon atoms representing $R_2$ or $R_3$ may be linear or branched. Examples of such a group include a normal- or iso-octyl group, a nonyl group, a decyl group, an undecyl group, a dodecyl group, a tridecyl group, a tetradecyl group, a pentadecyl group, and a hexadecyl group.

Specific examples of the compound (II) include dioctyldimethylammonium chloride, octyldecyldimethylammonium chloride, didecyldimethylammonium chloride, dicetyldimethylammonium chloride, and dilauryldimethylammonium chloride. Among these, didecyldimethylammonium chloride is most preferable.

The compound (II) has an eradicating activity against pathogens other than the coccidians, for example, viruses, bacteria, and fungi, and is useful as a disinfecting ingredient targeting thereto. Meanwhile, as described above, the compound (I) is effective for disinfection against coccidia.

The compound (I) and the compound (II) do not inhibit each other even when they are mixed, and respectively effectively act as disinfectants against target pathogens. Thus, a wide range of pathogens can be effectively eradicated in one operation by using a mixture of the compound (I) and the compound (II) mixed in advance or at the time of the use for the disinfection subject or disinfection subject area.

The compound (II) also serves as a surfactant ingredient and has a foaming property. Thus, by mixing the compound (I) and the compound (II), the mixture can be foamed and sprayed by using a foaming nozzle or the like even when an additional surfactant is not added or when the added amount of the surfactant is reduced.

The disinfection formulation of the present invention is basically used as a liquid formulation.

As described above, the concentration of the compound (I) in the disinfection formulation of the present invention is preferably 1 to 50,000 mg/L, more preferably 10 to 20,000 mg/L, yet more preferably 100 to 10,000 mg/L, still more preferably 150 to 5,000 mg/L, and most preferably 200 to 1,000 mg/L in terms of the final concentration (the concentration at the time of use).

The concentration of the compound (II) in the disinfection formulation of the present invention is preferably 1 to 20,000 mg/L and more preferably 10 to 500 mg/L in terms of the final concentration (the concentration at the time of use).

Thus, by using a high concentration of the compound (II), for example, by adjusting the concentration thereof to a final concentration (the concentration at the time of use) of 0.5 to 20 g/L, the mixture can be foamed and sprayed even when an additional surfactant is not added or when the added amount of the surfactant is reduced.

The disinfection formulation of the present invention can be prepared by, for example, mixing a solution dissolving the compound (I) and a solution dissolving the compound (II) in advance or at the time or use. Examples of the solvent for the compound (II) include alcohol, propylene glycol, polyethylene glycol, methyl cellulose, acetone, and DMSO.

Additives other than the compound (I) and the compound (II) in the disinfection formulation of the present invention, the disinfection subjects, the usage, etc., are the same as those for the anticoccidial disinfection formulation of the present invention.
<Disinfection Method>

The present invention encompasses all of anticoccidial disinfection methods for poultry houses and livestock barns, the methods involving using the anticoccidial disinfection formulation and the disinfection formulation of the present invention.

The coccidians can be effectively eradicated by using the anticoccidial disinfection formulation that contains the compound (I) in a poultry house or a livestock barn.

Thus, a wide range of pathogens can be effectively eradicated by using a disinfection formulation containing the compound (I) and the compound (II).

The disinfection formulation of the present invention is effective for disinfecting the floors and walls of the poultry house or the livestock barn, the articles installed or placed in these facilities, and the tools and machines used in the operation in these facilities, and can be used as a disinfection solution to be placed in a footbath provided at the doorways of these facilities.

For example, a liquid formulation of the present invention is prepared in advance or at the time of the use, and the disinfection subject or the disinfection subject area may be disinfected by wiping with a cloth or the like saturated with the disinfection solution, or the disinfection solution may be sprayed, atomized with an atomizer, or foamed by using a foaming nozzle or the like so as to disinfect the disinfection subject or the disinfection subject area. Alternatively, when the formulation is in a powder form, the formulation may be dispersed or sprayed directly toward the disinfection subject or the disinfection subject area. The amount of the active ingredients used and the like are as described above.

EXAMPLES

Example 1

In Example 1, the sporulation inhibitory activity of the allyl isothiocyanate against the coccidian oocysts was studied.

A chicken was infected with sporulated oocysts of a field strain of a coccidium (scientific name: "*Eimeria tenella*"), feces were collected seven days after the infection, and unsporulated oocysts in the feces were separated and purified to be used as sample materials.

As a testing substance, WASAOURO (registered trademark, produced by Mitsubishi-Chemical Foods Corporation, a powder formulation containing 10 wt % of allyl isothiocyanate, the same applies hereinafter) was dissolved in purified water to prepare a 5 mg/mL WASAOURO solution. To 10 mL of the WASAOURO solution, 1 mL (1/10 of the amount of the solution) of an unsporulated oocyst suspension (number of oocysts: $2.1 \times 10^5$ oocysts/mL) was added, and the mixture was sealed airtight with a stopper and was allowed to sensitize at 25° C. for one hour.

After completion of the sensitization, the supernatant was centrifugally removed (2,000 rpm, 5 minutes), the residue was centrifugally washed with a 0.5% neutral washing liquid four times (2,000 rpm, 5 minutes), and, after the supernatant was removed, a 2% potassium bichromate aqueous solution was added. While keeping the oocysts suspending in the solution, the oocysts were cultured at 25° C. for 5 days.

After the culturing, 500 oocysts among all oocysts were observed with a microscope, the number of oocysts that had undergone sporulation (sporulated oocysts) in 500 was counted, and the sporulation rate was calculated.

As a negative control, experiments were conducted by the same method and procedure except that the WASAOURO solution was replaced by purified water, and the number of sporulated oocysts and the sporulation rate were obtained.

As a positive control, experiments were conducted by the same method and procedure except that the WASAOURO solution was replaced by a TRIKIL solution, and the number of sporulated oocysts and the sporulation rate were obtained.

TRIKIL (registered trademark, produced by Tamura-seiyaku Corp) is a complex ortho agent containing orthodichlorobenzene, didecyldimethylammonium chloride, and chlorocresol, and has an eradicating activity against coccidian oocysts.

In this example, a TRIKIL solution diluted 100 folds with purified water was used according to the amount of the formulation used.

The results are shown in Table 1.

TABLE 1

| Testing substance | Number of sporulated oocysts (Oocysts) | Sporulation rate (%) |
|---|---|---|
| WASAOURO 5 mg/mL | 0/500 | 0% |
| Purified water (Negative control) | 462/500 | 92.4% |
| TRIKIL (Positive control) | 144/500 | 28.8% |

As shown in Table 1, WASAOURO (allyl isothiocyanate) was proven to prominently suppress sporulation of the oocysts. The sporulation inhibitory activity thereof was notable even in comparison with TRIKIL having high efficacy.

Example 2

In Example 2, the concentration that is effective for the sporulation inhibitory activity of allyl isothiocyanate was investigated, and whether the sporulation inhibitory activity was maintained even when allyl isothiocyanate was mixed with other disinfectants was studied.

As the testing substance for investigating the effective concentration, 1 mg/mL, 0.75 mg/mL, and 0.5 mg/mL WASAOURO solutions were respectively prepared by the same procedure as in Example 1.

As the testing substance mixed with other disinfectants, WASAOURO/CLEAKIL mixed solutions (WASAOURO: 1 mg/mL, 0.75 mg/mL, and 0.5 mg/mL, CLEAKIL: 2 µL/mL) were prepared. Note that CLEAKIL (registered trademark, produced by Tamura-seiyaku Corp) is a disinfection formulation containing 10 g of didecyldimethylammonium chloride per 100 mL, and has an disinfecting activity against a wide range of pathogens other than coccidia, such as viruses, bacteria, and fungi.

In this example, mixing was conducted according to the amount of the formulation used so that the final concentration was a dilution ratio of 500.

Experiments were conducted by the same method and procedure as in Example 1 except that the testing substance was changed, and the number of sporulated oocysts and the sporulation rate were obtained.

The results are shown in Table 2.

TABLE 2

| Testing substance | Number of sporulated oocysts (Oocysts) | Sporulation rate (%) |
|---|---|---|
| WASAOURO 1 mg/mL | 59/500 | 11.8% |
| WASAOURO 0.75 mg/mL | 94/500 | 18.8% |
| WASAOURO 0.5 mg/mL | 101/500 | 20.2% |
| WASAOURO 1 mg/mL + CLEAKIL | 20/500 | 4.0% |

TABLE 2-continued

| Testing substance | Number of sporulated oocysts (Oocysts) | Sporulation rate (%) |
|---|---|---|
| WASAOURO 0.75 mg/mL + CLEAKIL | 105/500 | 21.0% |
| WASAOURO 0.5 mg/mL + CLEAKIL | 178/500 | 35.6% |
| Purified water (Negative control) | 465/500 | 93.0% |
| TRIKIL (Positive control) | 116/500 | 23.2% |

As shown in Table 2, even when the WASAOURO concentration was reduced to as low as 0.5 mg/mL (concentration of allyl isothiocyanate: 50 mg/L), the sporulation rate was 20.2%, and a sporulation inhibitory activity substantially comparable to that of TRIKIL, namely, the positive control, was exhibited.

Even when WASAOURO was mixed with CLEAKIL, the sporulation inhibitory activity against coccidian oocysts was not mitigated and was effectively maintained.

Example 3

In Example 3, oocysts taken from feces of a cow with coccidiosis was used as the sample material to study the sporulation inhibitory activity of allyl isothiocyanate.

Feces of one cow exhibiting diarrhea due to coccidiosis were taken and were frozen and stored for 3 days; subsequently, unsporulated oocysts were separated from the feces and purified by a sucrose suspension method and used as the sample material. Results of the microscopic observation found that the separated oocysts were all coccidia of the genus *Eimeria* based on their forms, and the infection was mixed infection involving at least three species.

As the testing substances, 10 mg/mL and 5 mg/mL WASAOURO solutions were respectively prepared by the same procedure as in Example 1, and, to 400 µL of the WASAOURO solution, 40 µL (1/10 of the amount of the solution) of an unsporulated oocyst suspension (number of oocysts: $2.0 \times 10^4$ oocysts/mL) was added, and the mixture was sealed airtight with a stopper and was allowed to sensitize at 25° C. for one hour.

After completion of the sensitization, the supernatant was centrifugally removed (2,000 rpm, 5 minutes), the residue was centrifugally washed with purified water four times (2,000 rpm, 5 minutes, and, after the supernatant was removed, a 2% potassium bichromate aqueous solution was added. While keeping the oocysts suspending in the solution, the oocysts were cultured at 25° C. for 3 days.

After the culturing, for each substance, 100 oocysts among all oocysts were observed with a microscope, the number of oocysts that had undergone sporulation (sporulated oocysts) in 100 was counted, and the sporulation rate was calculated.

As a negative control, experiments were conducted by the same method and procedure except that the WASAOURO solution was replaced by purified water, and the number of sporulated oocysts and the sporulation rate were obtained.

The results are shown in Table 3.

TABLE 3

| Testing substance | Number of sporulated oocysts (Oocysts) | Sporulation rate (%) |
|---|---|---|
| WASAOURO 10 mg/mL | 0/100 | 0% |
| WASAOURO 5 mg/mL | 0/100 | 0% |
| Purified water (Negative control) | 99/100 | 99.0% |

As shown in Table 3, compared to the negative control, the sporulation rate was 0% in both cases that used the 10 mg/mL and 5 mg/mL WASAOURO solutions as the testing substances. This proves that WASAOURO (allyl isothiocyanate) has a sporulation inhibitory activity against coccidian oocysts in cows. Moreover, the sporulation inhibitory activity was confirmed against all of the three species of coccidia that were mixed in the feces of the cow.

Example 4

In Example 4, oocysts taken from feces of a cow with coccidiosis were used as the sample material to study the concentration of allyl isothiocyanate effective for the sporulation inhibitory activity.

As in Example 3, feces of one cow exhibiting diarrhea due to coccidiosis were taken and were frozen and stored for 1 day; subsequently, unsporulated oocysts were separated from the feces and purified by a sucrose suspension method and used as a sample material. Results of the microscopic observation found that the separated oocysts were all coccidia of the genus *Eimeria* based on their forms, and the infection was mixed infection involving at least three species.

As the testing substances for studying the effective concentration, 0.5 mg/mL, 1 mg/mL, 2 mg/mL, and 10 mg/mL WASAOURO solutions were respectively prepared by the same procedure as in Example 1, and, to 200 µL of the WASAOURO solution, 20 µL (1/10 of the amount of the solution) of an unsporulated oocyst suspension (number of oocysts: about $1.0 \times 10^4$ oocysts/mL) was added, and the mixture was sealed airtight with a stopper and was allowed to sensitize at 25° C. for one hour.

After completion of the sensitization, culturing was carried out by the same procedure as in Example 3, and, for each substance, 100 oocysts among all oocysts were observed with a microscope. The number of oocysts that had undergone sporulation (sporulated oocysts) in 100 was counted, and the sporulation rate was calculated.

As a negative control, experiments were conducted by the same method and procedure except that the WASAOURO solution was replaced by purified water, and the number of sporulated oocysts and the sporulation rate were obtained.

As a positive control, experiments were conducted by the same method and procedure except that the WASAOURO solution was replaced by a TRIKIL solution, and the number of sporulated oocysts and the sporulation rate were obtained. Note that, as in Example 1, the TRIKIL solution was prepared by diluting TRIKIL 100 folds with purified water.

The results are shown in Table 4.

TABLE 4

| Testing substance | Number of sporulated oocysts (Oocysts) | Sporulation rate (%) |
|---|---|---|
| WASAOURO 0.5 mg/mL | 40/100 | 40.0% |
| WASAOURO 1 mg/mL | 15/100 | 15.0% |
| WASAOURO 2 mg/mL | 0/100 | 0% |
| WASAOURO 10 mg/mL | 0/100 | 0% |
| Purified water (Negative control) | 98/100 | 98.0% |
| TRIKIL (Positive control) | 46/100 | 46.0% |

As shown in Table 4, the sporulation inhibitory activity against coccidian oocysts in cows was observed to be dependent on the WASAOURO concentrations.

Even when the concentration of the WASAOURO solution was 0.5 mg/mL, better results were obtained compared to TRIKIL, which was the positive control. When the concentration of the WASAOURO solution was 2 mg/mL, the sporulation rate was 0%. Moreover, the sporulation inhibitory activity was confirmed against all of the three species of coccidia that were mixed in the feces of the cow.

Example 5

In Example 5, oocysts taken from feces of a cow with coccidiosis were used as the sample material to study whether the sporulation inhibitory activity was maintained even when a mixture containing other disinfectant was used.

As in Example 3, feces of one cow exhibiting diarrhea due to coccidiosis were taken and were frozen and stored for 1 day; subsequently, unsporulated oocysts were separated from the feces and purified by a sucrose suspension method and used as a sample material. Results of the microscopic observation found that the separated oocysts were all coccidia of the genus *Eimeria* based on their forms, and the infection was mixed infection involving at least three species.

As the testing substances that are mixture with other disinfectants, WASAOURO/CLEAKIL mixed solutions (WASAOURO: 0.5 mg/mL, 1 mg/mL, and 2 mg/mL, CLEAKIL: 2 μL/mL) were respectively prepared by the same procedure as in Example 2, and, to 500 μL of the mixed solution, 50 μL (1/10 of the amount of the solution) of an unsporulated oocyst suspension (number of oocysts: about $1.7 \times 10^4$ oocysts/mL) was added, and the mixture was sealed airtight with a stopper and was allowed to sensitize at 25° C. for one hour.

After completion of the sensitization, culturing was carried out by the same procedure as in Example 3, and, for each substance, 100 oocysts among all oocysts were observed with a microscope. The number of oocysts that had undergone sporulation (sporulated oocysts) in 100 was counted, and the sporulation rate was calculated.

As a negative control, experiments were conducted by the same method and procedure except that the WASAOURO solution was replaced by purified water, and the number of sporulated oocysts and the sporulation rate were obtained.

As a positive control, experiments were conducted by the same method and procedure except that a WASAOURO solution (10 mg/mL) not mixed with CLEAKIL was used, and the number of sporulated oocysts and the sporulation rate were obtained.

As in Example 4, experiments were conducted by the same method and procedure for a TRIKIL solution also, except that the WASAOURO solution was replaced by a TRIKIL solution, and the number of sporulated oocysts and the sporulation rate were obtained.

The results are shown in Table 5.

TABLE 5

| Testing substance | Number of sporulated oocysts Oocysts) | Sporulation rate (%) |
|---|---|---|
| WASAOURO 0.5 mg/mL + CLEAKIL | 45/100 | 45.0% |
| WASAOURO 1 mg/mL + CLEAKIL | 15/100 | 15.0% |
| WASAOURO 2 mg/mL + CLEAKIL | 0/100 | 0% |
| WASAOURO 10 mg/mL | 0/100 | 0% |
| Purified water (Negative control) | 98/100 | 98.0% |
| TRIKIL (Positive control) | 47/100 | 47.0% |

As shown in Table 5, even when WASAOURO and CLEAKIL were mixed, the sporulation inhibitory activity against coccidian oocysts in cows was not mitigated and was effectively maintained.

Moreover, even when WASAOURO and CLEAKIL were mixed, the sporulation inhibitory activity was confirmed against all of the three species of coccidia that were mixed in the feces of the cow.

Although the present invention has been described in detail above through particular embodiments and examples, it is natural for a person skilled in the art that various modifications are possible without departing from the intension and the scope of the present invention.

The present application is based on Japanese Patent Application No. 2017-220780 filed on Nov. 16, 2017, the entire contents of which are incorporated herein by reference.

The invention claimed is:

1. A disinfection formulation, comprising:
a aqueous mixture of active ingredients consisting of 200 mg/L or greater of a compound of formula (I) and from 10 to 500 mg/L of a compound of formula (II):

wherein $R_1$ represents an alkenyl group having 2 to 8 carbon atoms, an alkyl group having 1 to 6 carbon atoms, an aryl group having 6 to 12 carbon atoms, an aralkyl group having 7 to 20 carbon atoms, or a cycloalkyl group having 3 to 6 carbon atoms:

wherein $R_2$ and $R_3$ each independently represent an alkyl group having 8 to 16 carbon atoms,
and a sporulation rate of coccidian oocysts in cows when contacted with the aqueous solution is 0%.

2. The disinfection formulation according to claim 1, wherein the compound of formula (II) is at least one selected from the group consisting of dioctyldimethylammnonium chloride, octyldecyldimethylammonium chloride, didecyldimethylammonium chloride, dicetyldimethylammonium chloride, and dilauryldimethylammonium chloride.

3. The disinfection formulation according to claim 1, wherein the compound of formula (I) is is allyl isothiocyanate.

4. The disinfection formulation according to claim 1, wherein the compound of formula (I) is is allyl isothiocyanate and the compound of formula (II) is didecyldimethylammonium chloride.

5. A method for disinfecting a poultry house or a livestock barn, comprising:
contacting the disinfection formulation according to claim 1 with the poultry house or livestock barn.

6. The disinfection method according to claim 5, wherein $R_1$ represents an alkenyl group having 2 to 6 carbon atoms.

7. The disinfection method according to claim 5, wherein the compound of formula (I) is allyl isothiocyanate.

8. The method for disinfecting a poultry house or a livestock barn according to claim 5, wherein the compound of formula (I) is allyl isothiocyanate and the compound of formula (II) is didecyldimethylammonium chloride.

\* \* \* \* \*